United States Patent [19]

Funderburk, Jr.

[11] 4,049,821

[45] Sept. 20, 1977

[54] METHOD OF TREATING ALLERGY

[75] Inventor: William Henry Funderburk, Jr., Richmond, Va.

[73] Assignee: A. H. Robins Company, Inc., Richmond, Va.

[21] Appl. No.: 685,576

[22] Filed: May 12, 1976

[51] Int. Cl.$^2$ .................................................. A61K 31/40
[52] U.S. Cl. ................................................... 424/274
[58] Field of Search ........................................ 424/274

[56] References Cited

U.S. PATENT DOCUMENTS

| 3,577,440 | 5/1971 | Lunsford et al. | 424/274 |
| 3,966,957 | 6/1976 | Cole, Jr. et al. | 424/274 |

Primary Examiner—Stanley J. Friedman

[57] ABSTRACT

Methods for ameliorating and controlling symptoms associated with asthma and other allergic phenomena employing compositions containing benzamides of 3-aminopyrrolidines are disclosed.

8 Claims, No Drawings

METHOD OF TREATING ALLERGY

The present invention relates to a method for ameliorating and controlling symptoms associated with asthma such as recurrent attacks of paroxysmal dyspnea, wheezing, coughing and a feeling of constriction, and to materials and compositions suitable therefor, and is more particularly concerned with the internal administration for this purpose of certain benzamides of 3-aminopyrrolidines which are disclosed in Lunsford et al. U.S. Pat. No. 3,577,440 issued May 4, 1971, and in allowed U.S. application Ser. No. 518,123 of Cale et al. filed Oct. 25, 1974 now U.S. Pat. No. 3,966,957.

The invention also contemplates the use of the aforementioned certain benzamides of 3-aminopyrrolidines in treating other allergic phenomena which includes, but is not limited to, allegic rhinitis, vernal conjunctivitis, aphthous stomatitis, gastrointestinal protein intolerance in infants and diarrhea which accompanies systemic mastocytosis.

Various systemic anti-allergy agents have been known long prior to this invention including, among others, aminophylline, theophylline, cortisosteroids, the disodium salt of 1,3-bis(2-carboxychromon-5-yloxy)-2-hydroxypropane and α-[(tert-bulylamino)methyl]-3,5-dihydroxybenzylalcohol sulfate. The efficacy of some has suffered from undesirable side effects while others which are effective prophylactically are not effective in acute manifestations of the allergic attack.

The present invention involves the discovery that certain benzamides of 3-aminopyrrolidines and especially N-(1-cyclohexyl-3-pyrrolidinyl)benzamides are capable of protecting sensitized guinea pigs from anaphylactic shock, without concurrently inducing local or systemic side effects. Compounds which are active in protecting guinea pigs from anaphylactic shock have been demonstrated to be generally effective in controlling or ameliorating the symptoms of allergy diseases in humans as, for example, asthma. Because of the high degree of effectiveness and relative freedom from untoward side effects of the compounds of the present invention, the systemic application thereof to persons having known allergy problems and in particular asthmatic problems is not only possible but clearly indicated.

The preferred compounds of the present invention are N-(1-cyclohexyl-3-pyrrolidinyl)benzamides. Compounds especially preferred are N-(1-cyclohexyl-3-pyrrolidinyl)-4-acetamidobenzamide, N-(1-cyclohexyl-3-pyrrolidinyl)-3-acetamidobenzamide and N-(1-cyclohexyl-3-pyrrolidinyl)-2-methoxy-5-sulfamoylbenzamide. N-(3-Pyrrolidinyl)benzamide is also a preferred compound.

It is therefore a primary object of the present invention to provide a method for ameliorating and controlling symptoms associated with asthma such as recurrent attacks of paroxysmal dyspnea, wheezing, coughing and a feeling of constriction by the internal administration of certain benzamides of 3-amino-pyrrolidines to warm blooded animals, including humans. Another object is to provide a method for treating other allergic phenomena by the internal administration of certain benzamides of 3-aminopyrrolidines to warm blooded animals, including humans. A still further object is to provide a method for ameliorating and controlling symptoms associated with asthma such as recurrent attacks of paroxysmal dyspnea, wheezing, coughing and a feeling of constriction and other allergic phenomena without concurrently inducing undesirable side effects by the internal administration of certain benzamides of 3-aminopyrrolidines.

Additional objects and advantages of the present invention will be apparent to one skilled in the art, and still others will become apparent from the following descriptions of the best mode of carrying out the present invention and examples thereof, and from the appended claims.

The compound which are useful in the present invention are illustrated generally by the following formula:

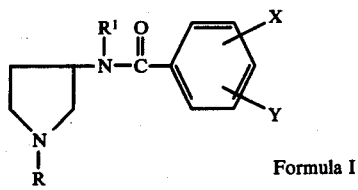

Formula I wherein;
R is hydrogen, lower cycloalkyl, phenyllower alkyl or lower alkyl,
$R^1$ is hydrogen or lower alkyl,
X is hydrogen, nitro, amino, acetamido, diloweralkylamino, hydroxy, lower alkoxy or loweralkylsulfonylamino, and
Y is hydrogen, nitro or sulfamoyl.

The invention also includes the pharmaceutically acceptable acid addition salts of the free bases of Formula I. The compounds of Formula I may be converted to and are conveniently stored in the form of pharmaceutically acceptable acid addition salts. Such salts also have improved water solubility. The free basic compounds of Formula I may be conveniently converted to said salts by reaction of the free base with the selected acid, preferably in the presence of an organic solvent inert to the reactants and reaction products under the conditions of the reaction.

Appropriate pharmaceutically acceptable acid addition salts are those derived from mineral acids such as hydrochloric acid, hydrobromic acid, hydroiodic acid, nitric acid, sulfuric acid, sulfamic acid and phosphoric acid; and organic acids such as acetic acid, citric acid, lactic acid, fumaric acid, maleic acid and tartaric acid.

In the definition of symbols in the foregoing Formula I and where they appear elsewhere throughout this specification the terms have the following significance.

The term "lower alkyl" as used herein includes straight and branched chain radicals of up to four carbon atoms inclusive and is exemplified by such groups as methyl, ethyl, n-propyl, isopropyl, butyl and isobutyl. The methyl radical is the preferred radical. The term "lower alkoxy" has the formula —O—lower alkyl.

The term "phenyllower-alkyl" includes groups such as benzyl, phenethyl, phenpropyl, α-methylbenzyl and the like. The lower alkyl moiety includes radicals of up to four carbon atoms inclusive.

The term "lower cycloalkyl" includes cyclic radicals having from three to seven carbon atoms inclusive and includes radicals such as cyclopropyl, cyclobutyl, cyclopentyl, methylcyclopentyl, cyclohexyl and cycloheptyl.

As mentioned hereinabove, compounds of the present invention were demonstrated to be active in preventing anaphylactic shock in sensitized guinea pigs. Guinea pigs of both sexes were sensitized by administering intraperioneally 1.0 ml. of horse serum followed by a second injection three days later of 0.1 ml. of horse serum by the same route. The guinea pigs were not used for 21 days after being sensitized. The activity of the compounds was determined by administering intraperitoneally minimal doses of each compound to sensitized guinea pigs thirty minutes prior to the intraperitoneal administration of 1.0 ml. of horse serum. When the compounds were given orally the horse serum was given one hour later. The time to death was recorded for each animal. All control animals died within 5 minutes. Five minutes was selected as the cut-off time to indicate activity of the compounds.

The compounds useful in practicing the present invention are summarized in Table 1. The compounds of Formula I are generally prepared by reacting together in an appropriate organic solvent a 3-aminopyrrolidine with a benzoyl halide, preferably a benzoyl chloride, said benzoyl chloride having the desired substituent or substituents on the phenyl moiety. For a more complete description of the compounds of the present invention given in Table 1 and the preparations thereof, the disclosures of Lunsford et al. U.S. Pat. No. 3,577,440 and allowed U.S. application Ser. No. 518,123 of Cale et al. filed Oct. 25, 1974, are hereby incorporated by reference as fully as though set forth herein.

Table 1

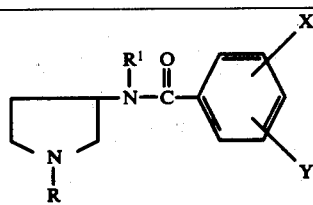

| Example | R | R¹ | X | Y | M.P. °C. | Salt |
|---|---|---|---|---|---|---|
| 1 | $C_6H_{11}$ | H | 4-$NH_2$ | H | 98–100 | Hydrate |
| 2 | $C_6H_{11}$ | H | H | H | 129–130 | |
| 3 | $C_6H_{11}$ | H | 3-$NO_2$ | 5-$NO_2$ | 159–161 | |
| 4 | H | H | H | H | 161–164 | Hydrochloride |
| 5 | $C_6H_{11}$ | H | 4-$CH_3CONH$ | H | 184–186 | |
| 6 | $C_6H_{11}$ | H | 4-$(CH_3)_2N$ | H | 138–141 | |
| 7 | $C_6H_{11}$ | H | 3-OH | H | 210–211 | |
| 8 | $C_6H_{11}$ | H | 2-$CH_3O$ | 5-$H_2NSO_2$ | 159–161 | Hydrochloride |
| 9 | $C_6H_{11}$ | $CH_3$ | 4-$CH_3CONH$ | H | 179–184 | Fumarate |
| 10 | $C_6H_{11}$ | H | 3-$NO_2$ | H | 142–145 | Fumarate |
| 11 | $C_6H_{11}$ | H | 3-$CH_3CONH$ | H | 148–150 | |
| 12 | $C_6H_{11}$ | H | 2-$NO_2$ | H | 218–220 | Hydrochloride |
| 13 | $C_6H_{11}$ | H | 4-$CH_3SO_2NH$ | H | 212–213 | |
| 14 | $C_6H_5CH_2$ | H | 4-$CH_3CONH$ | H | 138–140 | |

Table 2 summarizes the effectiveness of the compounds of the present invention summarized in Table 1 in preventing anaphylactic shock in sensitized guinea pigs using the procedure described hereinabove.

Table 2

| Example | Dose mg/kg | Route | No. Protected No. Treated |
|---|---|---|---|
| 1 | 50 | IP | 2/2 |
|   | 50 | PO | 1/2 |
| 2 | 50 | IP | 2/2 |
|   | 50 | PO | 0/1 |
| 3 | 50 | IP | 2/2 |
|   | 50 | PO | 2/2 |
|   | 25 | PO | 0/2 |
| 4 | 50 | IP | 2/2 |
|   | 100 | PO | 2/2 |
|   | 50 | PO | 2/2 |
|   | 25 | PO | 1/2 |
| 5 | 50 | IP | 2/2 |
|   | 20 | IP | 1/2 |

Table 2-continued

| Example | Dose mg/kg | Route | No. Protected No. Treated |
|---|---|---|---|
|   | 100 | PO | 2/2 |
|   | 50 | PO | 3/3 |
|   | 25 | PO | 3/3 |
|   | 20 | PO | 1/3 |
|   | 15 | PO | 1/3 |
| 6 | 50 | IP | 2/2 |
| 7 | 50 | IP | 2/2 |
|   | 50 | PO | 0/2 |
| 8 | 50 | IP | 2/2 |
|   | 100 | PO | 2/3 |
|   | 50 | PO | 1/3 |
| 9 | 50 | IP | 2/4 |
| 10 | 50 | IP | 1/2 |
| 11 | 50 | IP | 2/2 |
|   | 50 | PO | 2/3 |
|   | 25 | PO | 2/4 |
|   | 20 | PO | 0/3 |
| 12 | 50 | IP | 2/2 |
|   | 50 | PO | 0/2 |
| 13 | 50 | IP | 1/2 |
| 14 | 50 | IP | 2/2 |
|   | 50 | PO | 2/2 |
|   | 25 | PO | 1/2 |

Effective quantities of any of the foregoing pharmacologically active compounds of Formula I may be administered to a living animal body, including humans, in any one of various ways, for example, orally as in capsules, tablets or elixirs, parenterally in the form of sterile solutions or suspensions, and in some cases intravenously, e.g., in the form of sterile isotonic solutions. They can also be administered by inhalation. The free basic compounds, while effective, are preferably formulated and administered in the form of their pharmaceutically acceptable acid addition salts for purposes of convenience of crystallization, increased solubility and the like.

Although very small quantities of the active materials of the present invention are effective when minor therapy is involved or in cases of administration to subjects having a relatively low body weight, unit dosages are usually 2.5 milligrams or above, and preferably five, ten, twenty-five or fifty milligrams of active ingredient. Five to twenty-five milligrams appears optimum per unit dose. Obviously, several unit dosages may be administered at about the same time.

The dosage form are conveniently and easily produced by combining the active compounds of the present invention with carriers, fillers, extenders and excipients such as are generally used in the preparation of pharmaceutical products which are to be taken orally or given parenterally, and which are collectively referred to herein simply as a pharmaceutical carrier. For oral preparations the compositions may be prepared by mixing the active ingredient with such common diluents as cellulose powder, cornstarch, lactose, talc, stearic acid, magnesium stearate, gums, and the like.

Where the product is to be administered parenterally, the pharmacologically active compound, preferably in the form of a pharmaceutically acceptable acid addition salt, may be associated with such carriers as water, saline solution, glucose solution and the like.

cm I claim:

1. A method for ameliorating and controlling symptoms associated with asthma which comprises internally administering to a living animal body in need thereof an effective amount of an allergy ameliorating benzamide of the formula:

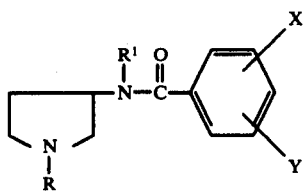

wherein;

R is hydrogen, lower cycloalkyl, phenyllower alkyl or lower alkyl,

R$^1$ is hydrogen or lower alkyl,

X is hydrogen, nitro, amino, acetamido, diloweralkylamino, hydroxy, lower alkyl or loweralkylsulfonylamino, and Y is hydrogen, nitro or sulfamoyl.

2. A method of claim 1 wherein the benzamide is in the form of a pharmaceutically acceptable acid addition salt and in unit dosage form.

3. A method of claim 2 wherein the unit dosage form contains from 2.5 milligrams to fifty milligrams of active compound.

4. A method of claim 3 wherein the benzamide compound is N-(1-cyclohexyl-3-pyrrolidinyl)-2-methoxy-5-sulfamoylbenzamide.

5. A method of claim 3 wherein the benzamide compound is N-(3-pyrrolidinyl)benzamide.

6. A method of claim 3 wherein the benzamide compound is N-(1-cyclohexyl-3-pyrrolidinyl)-3-acetamidobenzamide.

7. A method for ameliorating and controlling symptoms associated with asthma which comprises internally administering to a living animal body in need thereof an effective amount of N-(1-cyclohexyl-3-pyrrolidinyl)-4-acetamidobenzamide or a pharmaceutically acceptable acid addition salt thereof.

8. A method of claim 7 wherein N-(1-cyclohexyl-3-pyrrolidinyl)-4-acetamiodbenzamide is in unit dosage form in an amount of from 2.5 milligrams to fifty milligrams.

UNITED STATES PATENT AND TRADEMARK OFFICE
CERTIFICATE OF CORRECTION

PATENT NO. : 4,049,821

DATED : Sept. 20, 1977

INVENTOR(S) : William Henry Funderburk, Jr.

It is certified that error appears in the above-identified patent and that said Letters Patent are hereby corrected as shown below:

Col. 6, line 6, change "lower alkyl" to read

--lower alkoxy--

Signed and Sealed this

Twenty-eighth Day of February 1978

[SEAL]

Attest:

RUTH C. MASON
*Attesting Officer*

LUTRELLE F. PARKER
*Acting Commissioner of Patents and Trademarks*